United States Patent [19]

Robins et al.

[11] Patent Number: 4,925,930
[45] Date of Patent: May 15, 1990

[54] SYNTHESIS AND ANTI-LEUKEMIC ACTIVITY OF ALKYL-1-($\beta$-D-RIBOFURANOSYL)[1,2,4]-TRIAZOLE-3-CARBOXIMIDATES

[75] Inventors: Roland K. Robins, Irvine; Ganesh D. Kini, Costa Mesa, both of Calif.

[73] Assignee: Nucleic Acid Research Institute, Costa Mesa, Calif.

[21] Appl. No.: 266,097

[22] Filed: Nov. 2, 1988

[51] Int. Cl.$^5$ .......................................... C07H 19/056
[52] U.S. Cl. ........................................................ 536/23
[58] Field of Search ........................................... 536/23

[56] References Cited

U.S. PATENT DOCUMENTS

| | | | |
|---|---|---|---|
| Re. 29,835 | 11/1978 | Witkowski et al. | 536/29 |
| 3,798,209 | 11/1978 | Witkowski et al. | 536/29 |
| 3,897,415 | 7/1975 | Robins et al. | 260/211.5 R |
| 3,948,885 | 4/1976 | Witkowski et al. | 260/211.5 R |
| 3,968,103 | 7/1976 | Robins et al. | 260/211.5 R |
| 3,976,545 | 8/1976 | Witkowski et al. | 536/23 |
| 3,984,396 | 10/1976 | Witkowski et al. | 536/23 |
| 3,991,078 | 11/1976 | Witkowski et al. | 536/23 |
| 4,138,547 | 2/1979 | Christensen et al. | 536/23 |
| 4,211,771 | 7/1980 | Witkowski et al. | 536/23 |

OTHER PUBLICATIONS

Ganesh D. Kini, et al., J. Med. Chem., 32, 1447 (1989).
Witkowski et al., J. Med. Chem., 16, 935 (1973).
Riley et al., J. Heterocyclic Chem., 34, 955 (1987).

*Primary Examiner*—Johnnie R. Brown
*Assistant Examiner*—Gary L. Kunz
*Attorney, Agent, or Firm*—Herb Boswell

[57] ABSTRACT

A novel class of alkyl-1-($\beta$-D-ribofuranosyl)[1,2,4]-triazole-3-carboximidates of the formula:

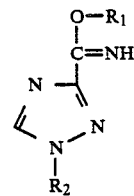

wherein $R_1$ is methyl or ethyl and $R_2$ is $\beta$-D-ribofuranosyl, are useful as anti-leukemic agents.

5 Claims, No Drawings

SYNTHESIS AND ANTI-LEUKEMIC ACTIVITY OF ALKYL-1-(β-D-RIBOFURANOSYL)[1,2,4]-TRIAZOLE-3-CARBOXIMIDATES

BACKGROUND OF THE INVENTION

This invention is directed to new alkyl-1-(β-D-ribofuranosyl) [1,2,4]triazole-3-carboximidates and their use as antitumor agents.

The nucleoside Ribavirin, i.e. 1-(β-D-ribofuranosyl)-[1,2,4]triazole-3-carboxamide, first reported by J. T. Witkowski; R. K. Robins; R. W. Sidwell; L. N. Simon; *J. Med. Chem.*, 1972, 15, 1150, is a broad spectrum antiviral agent of considerable interest. The antiviral activity of Ribavirin and its clinical applications have been reviewed in "Ribavirin, A Broad Spectrum Antiviral Agent", R. A. Smith; W. Kirkpatrick, Eds., Academic Press, New York (1980); "Clinical Applications of Ribavirin", R. A. Smith; V. Knight; J. A. D. Smith, Eds., Academic Press, New York (1984); and R. W. Sidwell; G. R. Revankar; R. K. Robins, in "Viral Chemotherapy", Vol. 2, D. Shugar, Ed., Pergamon Press, New York (1985), pp 49–108. Further this compound and certain related compounds are described in U.S. Pat. Nos. Re. 29,835, 3,976,545 and 4,211,771.

J. B. McCormick; J. P. Getchell; S. W. Mitchell; D. R. Hicks, 1984, *Lancet*, ii, 1367 have reported that ribavirin inhibits the replication of HIV in human T lymphocytes at 50 μg/mL. Several derivatives of ribavirin have been synthesized including 1-(β-D-ribofuranosyl)[1,2,4]triazole-3-carboxamidine hydrochloride first reported as an antiviral agent by J. T. Witkowski; R. K. Robins; G. P. Khare; R. W. Sidwell, *J. Med. Chem.* 1973, 16, 937.

Other nucleosides are useful as cancer chemotherapeutic agents. These include the antimetabolites 6-mercaptopurine, 6-thioguanosine and 5-bromouracil. 6-Mercaptopurine first found to be active against adenocarcinoma is presently utilized as the drug of choice in the treatment of leukemia.

Essentially all effective chemotherapeutic agents require repeated dosing in order to progressively diminish and kill the neoplastic cell populations affecting the host. During these repeated administrations of the chemotherapeutic agent it is further advantageous for the agent to not develop resistant cell lines. Because of the development of resistant cells by drugs presently used in the treatment of many neoplastic disease states, combinations of drugs are usually utilized. Thus, as resistant cells develop to a first drug, treatment with a second or further drug is often made in an attempt to effectively treat the drug resistant neoplastic cells.

In order to expand the arsenal of drugs available to treat neoplastic diseases, new chemotherapeutic drugs are continuously being sought.

BRIEF DESCRIPTION OF THE INVENTION

The present invention relates to a novel class of alkyl-1-(β-D-ribofuranosyl)[1,2,4]triazole-3-carboximidates useful as antitumor agents.

In accordance with one aspect of this invention, disclosed are compounds of the formula:

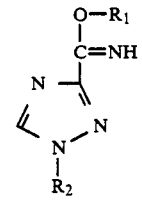

wherein $R_1$ is methyl or ethyl and $R_2$ is β-D-ribofuranosyl.

The compounds of the invention are useful as anti-leukemic agents. As such the compounds of the invention are useful in treating leukemias including lymphoblastic and myeloid leukemias.

Additionally, in accordance to the invention, a composition for the treatment of leukemias in an inflicted host as, for example a mammalian host (i.e. a warm blooded host), contains as its active ingredient a therapeutically effective amount of a compound selected from the above formula.

Further, in accordance with the invention, leukemias in a host mammal are treated by administering to the mammal in need thereof, a pharmaceutical composition containing as the active ingredient therein a therapeutically effective amount of a compound of the above formula admixed with a diluent amount of a physiologically tolerable carrier.

Particularly useful as anti-leukemic agents are the compounds methyl-1(β-D-ribofuranosyl)[1,2,4]triazole-3-carboximidate and ethyl-1(β-D-ribofuranosyl)[1,2,4]-triazole-3-carboximidate.

The methods of the invention and the compositions of the invention used therein, are effective in bringing about regression, palliation, inhibition of growth, and remission of leukemic malignancies.

For use in pharmaceutical compositions of the invention, a pharmaceutical carrier would be utilized. Preferable, the pharmaceutical carrier would be chosen to allow for administration of a suitable concentration of the active compounds of the invention either by oral administration, ophthalmic administration, topical administration, suppository administration or by suitable injection as a solution or suspension into the effected host. The dose and the choice of administration of the active compounds of the invention would depend upon the host harboring the malignancy and the type of malignancy. For injection, the active compounds of the invention could be administered intravenously, intramuscularly, intracerebrally, subcutaneously or intraperitoneally.

Compounds of the invention are also useful as intermediates in the preparation of the above referenced 1-(β-D-ribofuranosyl)[1,2,4]triazole-3-carboxamidine hydrochloride.

DETAILED DESCRIPTION OF THE INVENTION

The compounds of the invention are prepared utilizing the reaction sequence outlined in Scheme I. Ribavirin (1) was acetylated using acetic anhydride and pyridine in quantitative yields. The tri-O-acetylated carboxamide (2) was subsequently dehydrated with phosphorus oxychloride and triethylamine in chloroform solution leading to the nitrile, 3-cyano-1-(β-D-ribofuranosyl)[1,2,4]triazole (3), in yields in excess of 90%.

Treatment of the nitrile (3) with sodium methoxide in methanol resulted in the hitherto unknown imidate (4). In a similar fashion, upon treatment of compound (3) with sodium ethoxide in ethanol, the hitherto unknown imidate (5) was obtained.

Compounds (4) and (5), while devoid themselves of cell culture antiviral activity, can also be used as intermediates to prepare the known antiviral compound 1-($\beta$-D-ribofuranosyl)[1,2,4]triazole-3-carboxamidine hydrochloride (6). This known antiviral compound is prepared as, for example, by treatment of compound (4) with methanolic ammonia in the presence of ammonium chloride. This method of synthesis is extremely facile for the synthesis of the amidine (6) from the imidates (4) or (5). Prior synthesis of the amidine compound (6) was accomplished by the glycosylation of 3-cyano-[1,2,4]triazole with 1,2,3,5-tetra-O-acetyl-D-ribofuranose followed by separation of the isomers by chromatography.

CHEMICAL PREPARATIONS

NMR data were obtained on an IBM NR-300 spectrometer in $(CD_3)_2SO$ or $CDCl_3$ solvents using the residual proton as internal reference. Melting points were obtained in open capillaries using a Haake-Buchler apparatus and are uncorrected. Combustion analyses were performed by Robertson Laboratories, Florham Park, NJ.

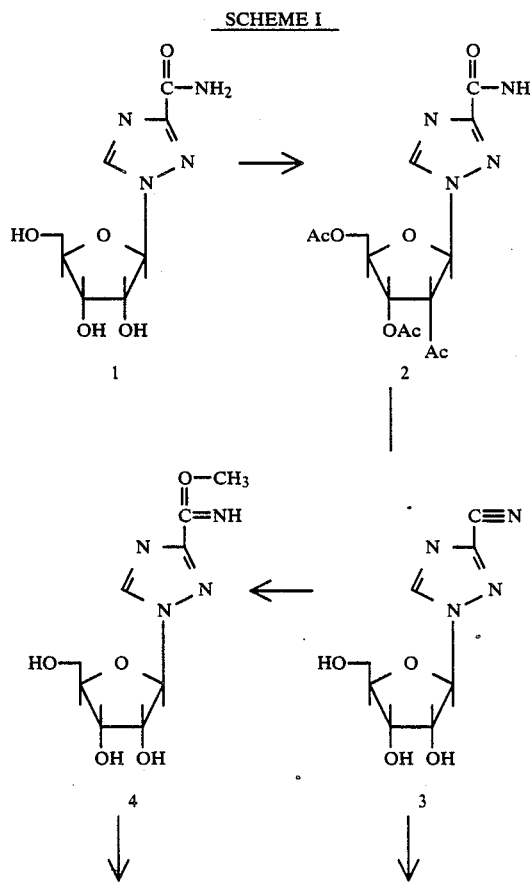

SCHEME I

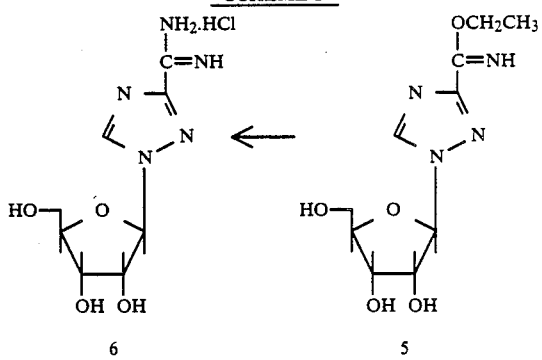

-continued
SCHEME I

EXAMPLE 1

2',3',5'-tri-O-acetyl-1-($\beta$-D-ribofuranosyl)[1,2,4]triazole-3-carboxamide (2)

A suspension of 1-($\beta$-D-ribofuranosyl)[1,2,4]triazole-3-carboxamide (28.4 g, 116.4 mmol) in acetic anhydride (200 mL) and pyridine (50 mL) was stirred at room temperature overnight. The resulting clear solution was concentrated in vacuo to yield a clear foam (43.1 g, quantitative). This foam was homogenous on tlc and used directly for the next step without purification. A small amount was purified by flash chromatography to yield an analytical sample. $^1H$ NMR (300 MHz, DMSO-$d_6$) 2.01, 2.08, 2.09 (3s, 9H, —$COCH_3$), 4.10 (m, 1H), 3.52 (m, 2H), 5.58 (t, 1H), 5.66 (m, 1H), 6.33 (d, 1H, J=3.0 Hz, $C_1H$), 7.73, 7.92 (2s, 2H, $CONH_2$), 8.86 (s, 1H, $C_5H$ triazole). Anal ($C_{14}H_{18}N_4O_8$) C, H, N. Calcd.: C, 45.41; H, 4.90; N, 15.13. Found: C, 45.32; H, 4.91; N, 15.12.

EXAMPLE 2

3-Cyano-2',3',5'-tri-O-acetyl-1-($\beta$-D-ribofuranosyl)-[1,2,4]triazole (3)

To a solution of compound (2) (43.1 g, 116.4 mmol) in chloroform (500 mL) was added triethylamine (244 mL) and the mixture cooled to 0° in an ice-salt bath. Phosphorus oxychloride (30.7 mL, 330 mmol) was added dropwise, with stirring and the solution allowed to warm to room temperature. After stirring at room temperature for 1 h, tlc (Hexane:acetone::3:1) indicated complete disappearance of starting material. The brown colored reaction mixture was concentrated to dryness in vacuo and the residue dissolved in chloroform (500 mL). This organic solution was washed with saturated aqueous sodium bicarbonate (3×200 mL), dried over anhydrous sodium sulfate and concentrated in vacuo. The residue was chromatographed over silica gel (flash chromatography) with 20% acetone in hexane to yield 33.14 g (81% from ribavirin) of pure compound (3) as an amorphous solid. This solid was identical in all respects to an authentic sample. mp 101°-103°; IR (Potassium bromide) $\eta$ 2250 (—CN), 1750 (C=O), $cm^{-1}$; 1H NMR (300 MHz, $CDCl_3$) $\delta$ 2.04, 2.06, 2.07 (3s, 9H, acetyl methyls), 4.15 (dd, 1H), 4.40 (m, 1H), 5.47 (t, 1H), 5.63 (dd, 1H), 5.95 (d, 1H, J=3.2 Hz, $C_1H$), 8.34 (s, 1H, $C_5H$ triazole).

EXAMPLE 3

Methyl-1-($\beta$-D-ribofuranosyl)[1,2,4]triazole-3-carboximidate (4)

To a suspension of compound (3) (8.7 g, 24.7 mmol) in methanol (100 mL) was added a molar solution of freshly prepared methanolic sodium methoxide (25 mL) and the mixture stirred at room temperature overnight. The clear colorless solution was treated with methanol washed Dowex H+ resin till the pH of the solution was 4. The resin was filtered, and the filtrate adsorbed on silica gel. It was then loaded on a silica gel column and chromatographed (flash chromatography) with 5% methanol in dichloromethane as eluent to yield pure 4 (4.0 g, 63.2%) as an amorphous solid. mp 150°–153°; $^1$H NMR (300 MHz, DMSO-d$_6$) $\delta$ 3.82 (s, 3H, —OCH$_3$), 5.8 (d, 1H, J=3.87 Hz, C$_1$H), 8.82 (s, 1H, C$_5$H triazole), 8.93 (s, 1H, imidate NH) and other sugar protons. Anal. (C$_9$H$_{14}$N$_4$O$_5$) C, H, N. Calcd.: C, 41.86; H, 5.46; N, 21.70. Found: C, 42.05; H, 5.29; N, 21.38.

EXAMPLE 4

Ethyl-1-($\beta$-D-ribofuranosyl)[1,2,4]triazole-3-carboximidate (5)

To a suspension of compound (3) (10.0 g, 28.4 mmol) in ethanol (100 mL) was added a 0.5 molar solution of freshly prepared ethanolic sodium ethoxide (20 mL) and the mixture stirred at room temperature overnight. The clear colorless solution was acidified with ethanol washed Dowex H+ resin to pH 5. The resin was filtered, and the filtrate adsorbed on silica gel. It was then loaded on a silica gel column and chromatographed (flash chromatography) with 5% ethanol in dichloromethane as eluent to yield pure 6 (5.0 g, 64.9%) as a foam; $^1$H NMR (300 MHz, DMSO-d$_6$) $\delta$ 1.31 (t, 3H, —CH$_2$CH$_3$), 5.8 (d, 1H, J=3.87, C$_1$H), 8.75 (s, 1H, C$_5$H triazole), 8.90 (s, 1H, imidate NH) and other sugar protons. Anal. (C$_{10}$H$_{16}$N$_4$O$_5$.0.5H$_2$O) C, H, N. Calcd.: C, 42.70; H, 6.09; N, 19.92. Found: C, 42.86; H, 5.83; N, 19.87.

EXAMPLE 5

1-($\beta$-D-ribofuranosyl)[1,2,4]triazole-3-carboxamidine hydrochloride (6)

To a suspension of compound (3) (4.0 g, 11.4 mmol) in methanol (100 mL) was added a molar solution of methanolic sodium methoxide (12 mL) and the mixture stirred at room temperature overnight. The solution was acidified to pH 4 with methanol washed Dowex H+ resin, the resin was filtered, and the filtrate concentrated to dryness in vacuo to yield compound (4) as the crude residue.

The compound (4) residue was dissolved in a minimum amount of methanol (15 mL) and transferred to a pressure bottle. Ammonium chloride (0.61 g, 11.4 mmol) and a solution of methanol saturated at 0° with dry ammonia gas (75 mL) were added, the bottle sealed and the solution stirred at room temperature overnight. The solution was concentrated to dryness in vacuo and the resulting residue crystallized from acetonitrile-ethanol to yield compound (6) as a crystalline solid (2.95 g, 93%). This sample was identical in all respects to an authentic sample prepared as per the above referenced J. T. Witkowski, et al., J. Med. Chem., 1973, 16, 937.

ANTITUMOR EVALUATIONS

In Vivo assessments of therapeutic efficacy and host toxicity with murine leukemia L1210 were made as detailed in M. Kuehl; D. I. Brixner; A. D. Broom; T. L. Avery; R. L. Blakley, Cancer Res., 1988, 48, 1481.

Briefly, BDF$_1$ female mice ($\approx$18 g) purchased from the Charles River Co. were inoculated ip on day 0 with 1×10$^6$ L1210 cells and treatment by ip bolus injection was initiated 24 hr later. Friend leukemia evaluations were performed similarly except female DBA$_2$ mice were inoculated with 0.2 ml of a 1:9 spleen homogenate formed by mincing spleen fragments in TC199. Drugs, solubilized in water immediately before use, were delivered in uniform volumes of 0.01 ml/gram mouse weight. Control mice received equivalent volumes of a 0.9% solution of NaCl.

The incidence of drug or leukemia related deaths, the postinoculation life span of mice that died, and drug modulation of leukemia induced splenomegaly were the end points by which responses to treatment were gauged. Temporal patterns of death and observations at necropsy examination were the major criteria for assigning deaths to leukemia or drug toxicity. Inoculum response data were used to calculate the body burdens of leukemia cells that survived treatment.

EXAMPLE 6

Antitumor Activity and Host Toxicity

The solubilities of compounds (4) and (5) in water are greatly dissimilar. As a result, the maximum dosage of compound (5) which could be delivered as a single bolus using a volumetric scheme of dosing was 3704 mg/kg while that of compound (4) was 480 mg/kg. Administered qd day 1 at those dosages, compound (5) was lethally toxic for L1210-inoculated mice (Table I) and compound (4) was not (Table II).

With the qd day 1 schedule of delivery, the maximum non-lethal dosage of compound (5) (1333 mg/kg) produced a T/C of 149 which, as gauged by inoculum response data, reflected a leukemic cell kill of 98.7%. Similar results were produced by qd day 1 treatment with 800 or 480 mg/kg of compound (5) with a decline of therapeutic efficacy at the 288 mg/kg level.

When administered qd days 1–7, lethal toxicity was produced by lower dosages of compound (5). On this schedule the increase in mean life span (T/C 144) produced by the maximum non-lethal dosage of compound (5) (288 mg/kg) was about the same as that observed when higher dosages were given less frequently. This finding indicates the anti-L1210 activity of compound (5) to be more dosage than schedule dependent.

The maximum soluble dosage of compound (4) (480 mg/kg) produced repeated T/C values of $\approx$115 when administered qd day 1. Because of limited water solubility relative to its biological activity, compound (4) was administered multiple times a day to determine its therapeutic potential. With qid day 1 delivery, the drug (480 mg/kg/injection) was lethally toxic but tid day 1 administration produced a T/C of 153 indicating a leukemic cell kill of >99%. Additional scheduling trials did not identify more effective therapy, suggesting that the anti-L1210 activity of compound (4) as that of compound (5) may be more dosage than schedule dependent.

TABLE I

Response of Mice Inoculated with L1210 Leukemia to
Ethyl-1-(β-D-ribofuranosyl)[1,2,4]triazole-3-carboximidate (5)

| Schedule of Administration | Dosage[a] (mg/kg) | Postinoculation Lifespan[b] (% T/C) | Residual Cell Population After Last Treatment[c] (% of control) |
|---|---|---|---|
| qd, day 1 | 3704 | 48 | tox |
| qd, day 1 | 2222 | 92 | tox |
| qd, day 1 | 1333 | 149 | 1.3 |
| qd, day 1 | 800 | 159 | 0.4 |
| qd, day 1 | 800 | 144 | 1.7 |
| qd, day 1 | 480 | 149 | 1.1 |
| qd, day 1 | 288 | 114 | 27.0 |
| qd, day 1-7 | 800 | 70 | tox |
| qd, day 1-7 | 480 | 134 | tox |
| qd, day 1-7 | 288 | 144 | 1.7 |

[a]All solutions were delivered ip (0.01 ml/gram mouse wt.) Control mice were injected with a 0.9% solution of NaCl.
[b]Treatment responses (6 mice/treatment group) presented as % T/C were calculated according to the equation, "Mean Life Span of Treated Mice/Mean Life Span of Control Mice × 100". The data presented were derived from 3 different studies in which 10 control mice lived 6.50 ± 0.53, 6.44 ± 0.53, and 6.60 ± 0.89 days. A T/C ≧ 125 is considered biologically significant. Tox indicates that 1 or more mice were killed by treatment.
[c]Calculations of residual leukemic cell populations weremade using inoculum-response data indicating therelationship between inoculum size and resultantpostinoculation life span.

TABLE II

Response of Mice Inoculated with L1210 Leukemia to
Methyl-1-(β-D-ribofuranosyl)[1,2,4]triazole-3-carboximidate (4)

| Schedule of Administration | Dosage[a] (mg/kg) | Postinoculation Lifespan[b] (% T/C) | Residual Cell Population After Last Treatment[c] (% of control) |
|---|---|---|---|
| qd, day 1 | 480 | 113 | 32 |
| qd, day 1 | 480 | 114 | 30 |
| qd, day 1 | 480 | 116 | 21 |
| bid, day 1 | 480 | 125 | 9 |
| tid, day 1 | 480 | 153 | 0.6 |
| qid, day 1 | 480 | 60 | tox |
| qd, day 1,4,7 | 480 | 119 | 73 |
| qd, day 1,3,5,7 | 480 | 121 | 46 |
| bid, day 1,3,5,7 | 480 | 162 | 12 |
| tid, day 1,3,5,7 | 480 | 76 | tox |
| qd, day 1-7 | 480 | 162 | 12 |
| qd, day 1-7 | 480 | 142 | 7 |
| qd, day 1-7 (po) | 480 | 97 | 139 |
| bid, day 1-7 | 480 | 101 | tox |
| tid, day 1-7 | 480 | 61 | tox |

[a]Except where otherwise indicated, all solutions were delivered ip (0.01 ml/gram mouse wt.). Control mice were injected with a 0.9% solution of Nacl.
[b]Treatment responses (6 mice/treatment group) presented as % T/C were calculated according to the equation, "Mean Life Span of Treated Mice/Mean Life Span of Control Mice × 100". The data presented were derived from 3 different studies in which 10 control mice lived 6.50 ± 0.53, 6.44 ± 0.53, and 6.60 ± 0.89 days. A T/C ≧ 125 is considered biologically significant. Tox indicates that 1 or more mice were killed by treatment.
[c]Calculations of residual leukemic cell populations were made using inoculum-response data indicating the relationship between inoculum size and resultant postinoculation life span.

EXAMPLE 7

Fried Leukemia Antitumor Activity

Compounds (4) and (5) were evaluated for activity against Friend leukemia. This is a erythroleukemia of viral origin. As per the results shown in Table III, Friend leukemia-related splenomegaly was significantly diminished by nontoxic dosing with compound (4) but not with compound (5).

TABLE III

Effect of treatment with
Methyl-1-(β-D-ribofuranosyl)[1,2,4]-triazole-3-carboximidate (4) or
Ethyl-1-(β-D-ribofuranosyl)[1,2,4]triazole-3-carboximidate (5) on
leukemia-related splenomegaly in DBA$_2$ Mice

| Drug Administered[a] | Schedule of Administration | Dosage (mg/kg) | Spleen Weight[b] (mg) |
|---|---|---|---|
| Control wo/tumor | qd, day 1,3,5,7,9,11 | — | 82 ± 11 |
| Control w/tumor | qd, day 1,3,5,7,9,11 | — | 1538 ± 561 |
| Compound (5) | | | |
| | qd, day 1,3,5,7,9,11 | 1333 | tox |
| | qd, day 1,3,5,7,9,11 | 800 | tox |
| | qd, day 1,3,5,7,9,11 | 480 | 1257 ± 185 |
| Compound (4) | | | |
| | qd, day 1,3,5,7,9,11 | 480 | 216 ± 60 (P < 0.01) |
| | bid, day 1,3,5,7,9,11 | 480 | tox |
| | qd, day 1,3,5,7,9,11 | 288 | 599 ± 133 (P < 0.02) |
| | bid, day 1,3,5,7,9,11 | 288 | 150 ± 53 (P < 0.005) |

[a]All solutions were delivered ip (0.01 ml/gram mouse wt.). Control mice were injected with a 0.9% solution of NaCl.
[b]Spleens were collected and weighed ≈24 hours after the last treatment. Statistical inference was by the Student t test.

As per Examples 6 and 7, compounds (4) and (5) exhibit significant antitumor activity in vivo. This is unexpected since contrary to this pronounced in vivo antitumor activity neither compound (4) nor compound (5) was cytotoxic for L1210 cells growing in vitro. Compounds (4)and (5) were also tested in vitro for their capacity to inhibit the growth of L1210 murine lymphocytic leukemia, WI-L2 human B lymphoblastic leukemia, and CCRF-CEM human T lymphoblastic leukemia in vitro. Again under in vitro cell culture conditions, neither compound demonstrated in vitro growth inhibition of the test cell lines.

Similarly, both compounds (4) and (5) were inactive when tested against parainfluenza type 3, adeno type 2, influenza A, rhino A, semliki forest, visna and herpes simplex type 2 viruses in cell culture.

The compounds of the invention can be given to a host in need thereof in appropriate formulations wherein the compounds comprise the active ingredient of the formulations. Thus a compound of the invention can be made up into injectables suitable for intravenous or other type injection into the host animal. Further it can be given in an appropriate oral formulation as for instance as an oral syrup preparation, an oral capsule or oral tablet. An additional route of administration might be as a suppository.

For an injectable the compound would be dissolved in a suitable solution as for instance in a sodium bicarbonate or other buffer. Such a solution would be filtered and added to appropriate ampoules or vials and sealed and sterilized.

As a syrup, the compound in buffered solution would be mixed with an appropriate syrup with mild stirring. For capsules the dry compound would be blended with appropriate fillers, binders or the like as for instance Lactose USP powder or Sterotex powder. For the preparation of tablets the compound of the invention would be mixed with suitable binders and fillers as for instance corn starch NF, Microcrystalline Cellulose, Sterotex powder and water and dried to a low water content. This would be followed by screening, milling, further screening and pressing into the appropriate tablets.

For suppositories, the compound would be dissolved into appropriate melts of Polyethylene Glycol as for instance Polyethylene Glycol 1540 and 8000 at 60° and formed into the suppositories by molding at 25°.

In addition to the above formulations, a compound of the invention could also be administered utilizing other delivery technique such as incorporating the compound of the invention with liposomes and the like.

Additionally, prodrug forms of the compounds of the invention could be utilized to facilitate dispensing, uptake, absorption, metabolic control and the like. One such prodrug would be the tri-acetate ester. Further prodrugs might allow for enzymatic conversion in vivo of analogs of the compound of the invention into the compound of the invention, e.g. the 5'-phosphate analog might be enzymatic converted.

We claim:

1. Methyl-1-(β-D-ribofuranosyl)[1,2,4]triazole-3-carboximidate.
2. Ethyl-1-(β-D-ribofuranosyl)[1,2,4]triazole-3-carboximidate.
3. A compound of the structure:

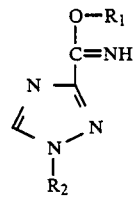

wherein $R_1$ is methyl or ethyl and $R_2$ is β-D-ribofuranosyl.

4. A compound of claim 3 wherein:
$R_1$ is methyl.
5. A compound of claim 3 wherein:
$R_1$ is ethyl.

* * * * *